United States Patent [19]

Hsiung

[11] 4,417,046
[45] Nov. 22, 1983

[54] PROCESS FOR ISOLATING OLIGONUCLEOTIDE PRODUCT FROM A COUPLING REACTION MIXTURE

[75] Inventor: Hansen M. Hsiung, Indianapolis, Ind.

[73] Assignee: Eli Lilly and Company, Indianapolis, Ind.

[21] Appl. No.: 295,419

[22] Filed: Aug. 24, 1981

[51] Int. Cl.³ .................. C07H 15/12; C07H 17/00
[52] U.S. Cl. .................................. 536/27; 536/28; 536/29
[58] Field of Search ................. 536/23, 27, 28, 29

[56] References Cited

U.S. PATENT DOCUMENTS

| | | | |
|---|---|---|---|
| 3,314,937 | 4/1967 | Vendrely et al. | 536/29 |
| 3,433,782 | 3/1969 | Kreiser | 536/28 |
| 3,534,017 | 10/1970 | Fujimoto et al. | 536/29 |
| 3,709,873 | 1/1973 | Fujimoto | 536/23 |
| 3,792,039 | 2/1974 | Erickson et al. | 536/29 |
| 4,210,746 | 7/1980 | Kerr et al. | 536/28 |

FOREIGN PATENT DOCUMENTS

| | | | |
|---|---|---|---|
| 675390 | 12/1963 | Canada | 536/29 |
| 461927 | 9/1975 | U.S.S.R. | 536/28 |

OTHER PUBLICATIONS

Sung et al., Can. J. Chem., vol. 60, No. 2, Jan. 15, 1982.
Agarwal et al., Journ. Amer. Chem. Soc. 95(6), pp. 2020-2021, (1973).
Ogilvie et al., Can. Journ. Chem., vol. 48, (1970), pp. 862-864.
Werstiuk et al., Can. Journ. Chem., vol. 54, No. 17, (1976), pp. 2689-2696.

*Primary Examiner*—Ethel G. Love
*Attorney, Agent, or Firm*—William C. Martens; Arthur R. Whale

[57] ABSTRACT

A polynucleotide product produced by coupling in the presence of a coupling agent (1) a nucleotide or oligonucleotide having a blocked 5'-hydroxyl group and a 3'-phosphate diester group and (2) a nucleotide or oligonucleotide having a blocked 3'-hydroxyl or a blocked 3'-phosphate diester group and a free 5'-hydroxyl group is recovered from the reaction mixture by addition of an organic solvent or mixture of organic solvents which precipitates the polynucleotide product from the reaction mixture while retaining the coupling agent in solution.

4 Claims, No Drawings

PROCESS FOR ISOLATING OLIGONUCLEOTIDE PRODUCT FROM A COUPLING REACTION MIXTURE

BACKGROUND OF THE INVENTION

With the advent of recombinant DNA methodology and especially in view of its evident commercial applicability, the ability to synthesize oligodeoxyribonucleotides of defined sequences has become increasingly important.

As now is very well recognized, RNA and DNA are polynucleotides referred to as nucleic acids. The polynucleotides, in turn, are composed of monomers (nucleotides). A nucleotide is a phosphate ester of the N-glycoside of a nitrogenous base and consists of a purine or a pyrimidine base, a pentose (D-ribose in RNA or 2'-deoxy-D-ribose in DNA), and a phosphate group.

Four nitrogenous bases are present in both DNA and RNA. The four present in DNA are:

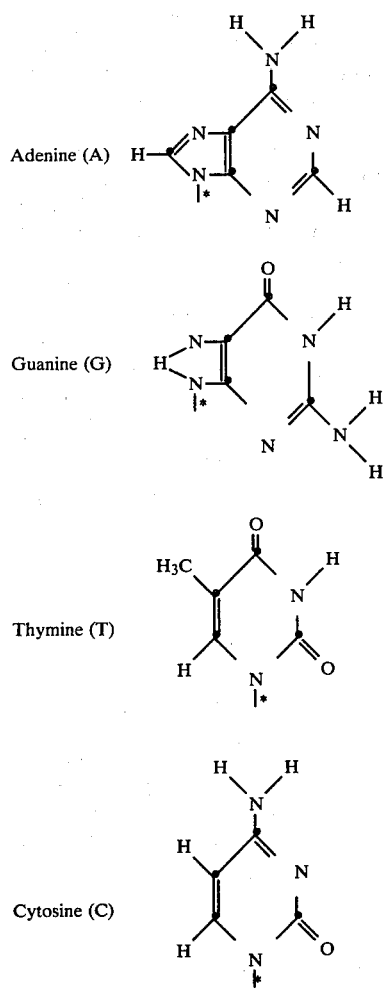

The nitrogenous bases in RNA differ from those in DNA only in that uracil (U) replaces thymine.

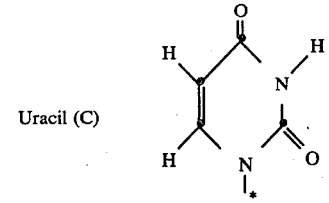

The combination of a nitrogenous base at the point of the asterisk (*) in the foregoing formulas with a ribose at its 1'-position is called a ribonucleoside (D-ribose) or a deoxyribonucleoside (2'-deoxy-D-ribose). The corresponding ribonucleotide or deoxyribonucleotide is produced by addition of a phosphate group at the 3'-position of the ribose.

The thus-defined suitably-blocked ribonucleotide or deoxyribonucleotide represents the basic building block in the synthesis of RNA or DNA, respectively. A standard and highly attractive method for synthesizing RNA or DNA is known in the literature as the "triester method". Using the synthesis of a polydeoxyribonucleotide as an example, the procedure involves coupling a mononucleotide or oligonucleotide having a 3'-phosphate diester with a mononucleoside, a blocked 3'-hydroxy oligonucleotide, a mononucleotide, or an oligonucleotide having an available 5'-hydroxyl group. This method can be represented schematically as follows:

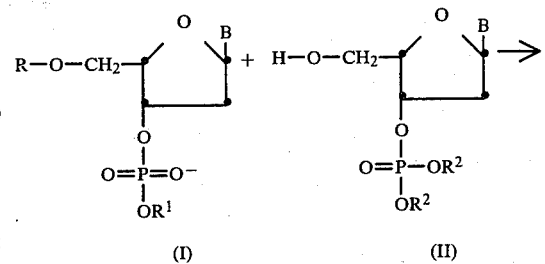

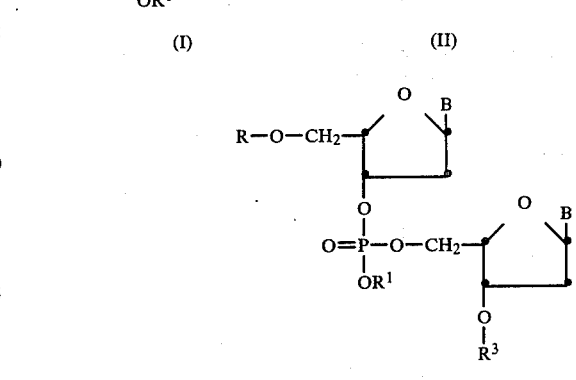

In the foregoing, B is a nitrogenous base selected from adenine, cytosine, guanine, and thymine, each of the first three having their reactive moieties blocked by suitable protecting groups; R is a blocking group for the 5'-hydroxyl; $R^3$ is a blocking group for the 3'-hydroxyl cleavable under alkaline conditions or a group of the formula

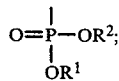

and $R^1$ and $R^2$ are selevtively removable groups which block the reactive phosphate moiety.

Additional discussion of the triester method can be found in various publications including, for example, Narang, S. A., Hsiung, H. M., and Brousseau, R., "Improved Phosphotriester Method for the Synthesis of Gene Fragments", *Methods in Enzymology*, Vol. 68, Academic Press, New York, N.Y., (1979), pp. 90-98; and Narang, S. A., Brosseau, R., Hsiung, H. M., and Michniewicz, J. J., "Chemical Synthesis of Deoxyoligonucleotides by the Modified Triester Method", *Methods in Enzymology*, Vol. 65, Academic Press, New York, N.Y. (1980), pp. 610-620.

The triester method described above, of course, has been applied in coupling two oligonucleotides, an oligonucleotide and a mononucleotide, or, as specifically illustrated above, two mononucleotides. Whatever the entities, the reaction involves the coupling of an available 5'-hydroxyl with a 3'-phosphate diester group. Moreover, the reactant containing the available 5'-hydroxyl can have a blocked terminal phosphate or such can be lacking (i.e., $R^3$ is a 3'-hydroxyl blocking group). The two reactants are coupled in the presence of a solvent, typically pyridine, and in the presence of a coupling agent, for example, 2,4,6-trimethylbenzenesulfonyl tetrazolide.

The product from the coupling reaction generally is recoverable from non-coupled nucleotide starting materials using standard and recognized conditions of chromatographic separation. However, in order to render the reaction mixture ready for chromatography, it has been necessary to eliminate amounts of residual coupling agent present in the reaction mixture.

The method heretofore used to render the reaction mixture ready for chromatographic purification involves a complex and tedious sequence initiated by aqueous decomposition of the coupling reagent. In addition to being complex and tedious, the recognized method, due to the conditions employed, generally results in measurable product degradation. In general, the work-up heretofore employed involves (1) addition of water to decompose the coupling agent, (2) concentration of the reaction mixture, (3) addition of chloroform, (4) washing with saturated sodium bicarbonate, (5) drying of organic phase, and (6) evaporation of organics. The residue then is ready for chromatographic purification.

A method for readily and rapidly placing product from a nucleotide coupling reaction into condition for chromatographic purification has now been discovered. It is to such a process that this invention is directed.

SUMMARY OF THE INVENTION

Thus, this invention is directed to a process for recovering from a reaction mixture polynucleotide product produced by coupling in the presence of a coupling agent (1) a nucleotide or oligonucleotide having a blocked 5'-hydroxyl group and a 3'-phosphate diester group and (2) a nucleotide or oligonucleotide having a blocked 3'-hydroxyl or a blocked 3'-phosphate diester group and a free 5'-hydroxyl group, which comprises adding to the reaction mixture an organic solvent or a mixture of organic solvents and precipitating polynucleotide product from the reaction mixture while retaining coupling agent in solution.

DETAILED DESCRIPTION OF THE INVENTION

As noted, this invention is directed to a process for facilitating recovery of polynucleotide product from a reaction mixture in which the product results from a nucleotide coupling reaction. In particular, this invention applies to the well-recognized triester method for synthesizing polynucleotides.

In any polynucleotide preparation, suitable blocking of otherwise reactive moieties is necessary. Thus, certain of the nitrogenous bases require blocking of their reactive amino groups. Typically, adenine and cytosine are benzoylated to protect their free amino groups, and guanine customarily is protected by an isobutyryl group. Thymine, since it has no free amino group, requires no protection. Of course, the foregoing are only examples of suitable blocking groups. Any of a wide range of other blocking groups can be employed.

The group R in the foregoing formulas represents a protecting group for the 5'-hydroxyl moiety. Preferably, the group is labile under mildly acidic conditions. Examples of such groups are tetrahydropyrenyl, 4-methoxytrityl, 4,4'-dimethoxytrityl (DMTr), and the like. 4,4'-Dimethoxytrityl is readily removed in mild acid, for example, 2% benzenesulfonic acid, and represents a preferred protecting group for the 5'-hydroxyl moiety.

The "triester method" is so-called because the coupled product is a phosphate triester. This, in turn, contemplates the use of nucleotide reactant having a partially-blocked 3'-phosphate group. The group $R^1$ used herein is intended to refer to a group that completes a suitable partial block. This group preferably is one that is removable under alkaline conditions. Examples of suitable groups are phenyl, o-chlorophenyl, 2,4-dichlorophenyl, p-chlorophenyl, p-nitrophenyl, o-nitrophenyl, 2,4-dinitrophenyl, p-mercaptophenyl, and the like. Preferably, $R^1$ is p-chlorophenyl.

A fully blocked nucleotide or the 3'-phosphate-containing terminal of a polynucleotide produced by the triester method contains a fully blocked phosphate of the formula

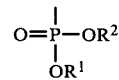

The group $R^2$ represents a group that can be selectively cleaved, generally under mild alkaline conditions. The current blocking group of choice is $\beta$-cyanoethyl. A blocked phosphate in which $R^1$ is p-chlorophenyl and $R^2$ is $\beta$-cyanoethyl is conveniently denoted OPCE.

It is possible that the 3'-terminal of a polynucleotide product lacks a phosphate in which case $R^3$, as hereinbefore described, is a 3'-hydroxyl blocking group cleavable under alkaline conditions. Suitable such groups are acetyl, benzoyl, p-methoxybenzoyl, and chloroacetyl. Preferably, the blocking group is benzoyl (Bz). Nucleotide coupling is carried out in the presence of a coupling agent. Suitable coupling agents are well recognized by those skilled in the art. Examples of suitable coupling agents are p-nitrobenzenesulfonyl triazolide, benzenesulfonyl triazolide, benzenesulfonyl 4-nitroimidazolide, 2,4,6-triisopropylbenzenesulfonyl 3-nitro-1,2,4-triazolide, 2,4,6-trimethylbenzenesulfonyl 3-nitro-1,2,4-triazolide, 1-(p-toluenesulfonyl) 4-nitroimidazolide, 2,4,6-trimethylbenzenesulfonyl tetrazolide, 2,4,6-triisopropylbenzenesulfonyl chloride, 2,4,6-trimethylbenzenesulfonyl chloride, 2,4,6-triisopropylbenzenesulfonyl tetrazolide, and the like. Preferably, the coupling agent is 2,4,6-triisopropylbenzenesulfonyl tetrazolide or 2,4,6-trimethylbenzenesulfonyl tetrazolide.

The coupling reaction is carried out in the presence of a suitable inert organic solvent under substantially anhydrous conditions. The current solvent of choice is pyridine.

Products that are readily recoverable in accordance with the process of this invention include polynucleotides having the formula

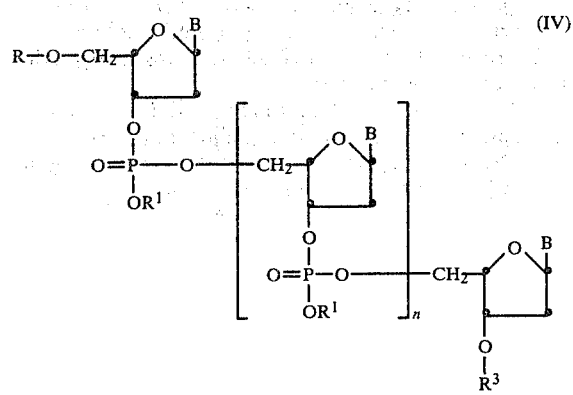

in which B, R, R$^1$, and R$^3$ are as hereinbefore defined and n is zero or an integer, generally not greater than about 20.

The reaction time required for coupling generally will be not greater than about 2 hours no matter what the size of the intended polynucleotide product. Determining any particular reaction time is a relatively easy matter since the extent of reaction can be monitored using any of a variety of analytical techniques including, for example, thin-layer chromatography, high performance liquid chromatography, and the like.

Upon completion of the coupling reaction, the polynucleotide product can be readily separated from the reaction mixture and placed in condition for chromatographic purification by the method which forms the basis of this invention. Before it is possible to chromatographically separate polynucleotide product from any residual nucleotide reactants, it is necessary to remove from the product mixture any residual amounts of coupling agent that may remain. Heretofore, this has been accomplished by aqueous decomposition of the coupling agent involving a series of cumbersome, tedious, and time-consuming extraction steps. Moreover, this methodology many times was accompanied by product degradation. These tedious steps are avoided by the method of this invention. By addition to the reaction mixture of an organic solvent or solvent mixture that selectively precipitates polynucleotide product and residual amounts of uncoupled nucleotide while retaining coupling agent in solution, it is possible to easily, quickly, and without product degradation render the mixture ready for final chromatographic purification.

The essential properties of the organic solvent or mixture of organic solvents employed in the process of this invention are (1) solubility of the coupling agent and (2) insolubility of the polynucleotide product. Substantially anhydrous ethers, such as diethyl ether, di-n-propyl ether, diisopropyl ether, tetrahydrofuran, and others of similar polarity, as well as mixtures comprising such ethers, are preferred for use in the process of this invention. A particularly preferred ether is ethyl ether. In general, mere addition to the reaction mixture of a large excess, usually about 10 to about 20 fold by volume based upon the volume of the reaction mixture, of any of the aforementioned ethers as well as others of similar characteristics produces immediate precipitation of the polynucleotide product. When n in the product depicted by formula IV in an integer, the addition of an ether alone will produce virtually complete precipitation of the polynucleotide product. When n is zero, although precipitation of the dinucleotide will occur, some product loss may be experienced. This loss can be minimized or eliminated by the use of a mixture of an ether and a low boiling aliphatic hydrocarbon such as pentane or hexane, the latter usually being present in an amount representing, on a volume basis, from about 25% to about 75% of the solvent mixture.

The following examples are provided to further illustrate the process of this invention. They are not intended to be limiting upon the scope thereof.

EXAMPLE 1

Synthesis of DMTrO-TG-OPCE

5'-O-Dimethoxytritylthymidine-3'-O-p-chlorophenyl-β-cyanoethyl phosphate (1.5 g. 1.9 mmol.) was dissolved in 20 ml. of anhydrous pyridine. t-Butylamine (about 3 ml.) was added dropwise to the above solution with stirring. The reaction was allowed to proceed for about 10 minutes after which decyanoethylation was complete as shown by silica gel thin-layer chromatography (solvent: 10% MeOH/CH$_2$Cl$_2$).

The reaction mixture was evaporated to dryness to remove pyridine, t-butylamine, and acrylonitrile. The dried reaction mixture was then redissolved in CH$_2$Cl$_2$ (20 ml.), and N-isobutyryldeoxyguanosine-3'-O-p-chlorophenyl-β-cyanoethyl phospate (0.93 g., 1.6 mmol. ) was added. The two protected mononucleotides were dried extensively in vacuo and redissolved in 10 ml. of anhydrous pyridine. The condensating agent, 2,4,6-trimethylbenzenesulfonyl tetrazolide (1.01 g., 4 mmol.), was added, and the reaction was allowed to proceed for one hour at ambient temperature. At the end of this period, the coupling reaction was shown to be complete by the disappearance of the 5'-hydroxyl reactant and appearance of an intense trityl positive spot of the dinucleotide (tlc: 10% MeOH/CH$_2$Cl$_2$).

The reaction mixture then was pipetted and transferred to 150 ml. of a 1:1 volume mixture of ether and hexane. A white precipitate containing the dinucleotide product formed and was collected by centrifugation. Thin-layer chromatography (10% MeOH/CH$_2$Cl$_2$) of the supernatant showed no dinucleotide product.

EXAMPLE 2

Synthesis of DMTrO-GGTA-OPCE

To 200 mg. of DMTrO-GG-OPCE were added approximately 4 ml. of dry pyridine and approximately 2 ml. of t-butyl amine. The decyanoethylation was complete after 10 minutes, as determined by tlc, and the mixture was evaporated to dryness in vacuo. The decyanoethylated dimer was combined with $1.21 \times 10^{-4}$ moles of HO-TA-OPCE, and the mixture was dried for 30 minutes in vacuo. To initiate coupling, 200 mg. of 2,4,6-trimethylbenzenesulfonyl tetrazolide and approximately 4 ml. of dry pyridine were added. Coupling was complete after one hour. The mixture then was stirred into two centrifuge tubes, each containing 40 ml. of ethyl ether. A precipitate of the tetramer formed. The tubes were centrifuged for four minutes, the ether was decanted, and the product was dissolved in dichloromethane, and the solution was evaporated to dryness. After purification on a silica plate in 25% acetone, 70% ethyl acetate, 5% water, 121 mg. (43.2%) of the title compound were recovered.

EXAMPLE 3

Synthesis of DMTrO-CGGACAGAGACA-OBz

To 56 mg. of DMTrO-CGGA-OPCE were added 2 ml. of pyridine and 1 ml. of t-butyl amine. After 10 minutes the reaction mixture was dried in vacuo. To the residue were added 52 mg. of HO-CAGAGACA-OBz, and the mixture was dried in vacuo for 30 minutes. To the mixture then were added 90 mg. of 2,4,6-trimethylbenzenesulfonyl tetrazolide and 0.5 ml. of dry pyridine. The coupling reaction was completed after one hour. The mixture then was stirred into a centrifuge tube containing 40 ml. of ethyl ether. After centrifuging for four minutes, the ether was decanted, and the product was dissolved in dichloromethane and, the solution was evaporated to dryness. Purification of 5/6 of the material on a silica plate in 25% acetone, 70% ethyl acetate, 5% water gave 40 mg. of the title compound (57.3% yield based upon purification of all of the product).

I claim:

1. A process for recovering from a reaction mixture polynucleotide product produced by coupling in the presence of a coupling agent (1) a nucleotide or oligonucleotide having a blocked 5'-hydroxyl group and a 3'-phosphate diester group and (2) a nucleotide or oligonucleotide having a blocked 3'-hydroxyl or a blocked 3'-phosphate diester group and a free 5'-hydroxyl group, which comprises adding to the reaction mixture an organic solvent or a mixture of organic solvents comprising a substantially anhydrous ether thereby precipitating polynucleotide product from the reaction mixture while retaining coupling agent in solution.

2. Process of claim 1, in which the substantially anhydrous ether is ethyl ether.

3. Process of claim 2, in which ethyl ether is used in combination with a low boiling aliphatic hydrocarbon.

4. Process of claim 3, in which the low boiling aliphatic hydrocarbon is pentane or hexane.

* * * * *